(12) United States Patent
Subramanyam

(10) Patent No.: US 8,313,733 B2
(45) Date of Patent: *Nov. 20, 2012

(54) ANTIBACTERIAL 5,5'-DISUBSTITUTED 3,3' DIALKOXY-2,2'-DIHYDROXY-1,1'-BIPHENYL

(75) Inventor: Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 164 days.

This patent is subject to a terminal disclaimer.

(21) Appl. No.: 12/390,862

(22) Filed: Feb. 23, 2009

(65) Prior Publication Data

US 2009/0155192 A1    Jun. 18, 2009

Related U.S. Application Data

(63) Continuation of application No. 11/374,834, filed on Mar. 14, 2006.

(51) Int. Cl.
*A61K 8/00* (2006.01)
(52) U.S. Cl. .......................... 424/48; 424/49
(58) Field of Classification Search ................ 424/48, 424/49
See application file for complete search history.

(56) References Cited

U.S. PATENT DOCUMENTS

| | | | |
|---|---|---|---|
| 3,429,963 A * | 2/1969 | Shedlovsky | 424/56 |
| 5,292,526 A | 3/1994 | Gaffar | |
| 5,356,615 A | 10/1994 | Gaffar | |
| 5,472,684 A | 12/1995 | Nabi et al. | |
| 6,342,205 B1 | 1/2002 | Niemi et al. | |
| 6,379,652 B1 * | 4/2002 | Liu et al. | 424/49 |
| 6,511,966 B2 | 1/2003 | Ghosh et al. | |
| 6,740,311 B2 | 5/2004 | White, Jr. et al. | |
| 6,977,082 B2 | 12/2005 | Seitz, Jr. et al. | |
| 7,196,117 B2 | 3/2007 | Beltran et al. | |
| 7,205,266 B2 | 4/2007 | Holderbaum et al. | |
| 2003/0049303 A1 * | 3/2003 | Ning et al. | 424/439 |
| 2006/0120975 A1 | 6/2006 | Scherl et al. | |
| 2006/0140880 A1 | 6/2006 | Subramanyam et al. | |
| 2006/0141072 A1 | 6/2006 | Arvanitidou et al. | |
| 2006/0233722 A1 | 10/2006 | Subramanyam | |

FOREIGN PATENT DOCUMENTS

| | | |
|---|---|---|
| EP | 0850912 | 7/1998 |
| EP | 1405851 | 4/2004 |
| JP | 07033649 | 2/1995 |
| JP | 09176074 * | 7/1997 |
| JP | 9278638 | 10/1997 |
| JP | 2000-169846 A | 6/2000 |
| JP | 2004292392 A2 | 10/2004 |
| KR | 20020004025 | 1/2002 |
| WO | 9710800 A2 | 3/1997 |
| WO | 0182922 A1 | 11/2001 |
| WO | 0185116 A2 | 11/2001 |
| WO | WO 2006/060145 | 6/2006 |

OTHER PUBLICATIONS

Silverman, Richard B. The Organic Chemistry of Drug Design and Drug Action. London; Academic Press, Inc, 1992.*
Fujisawa et al., "Application of Bis-Eugenol to A Zinc Oxide Eugenol Cement," Journal of Dentistry, (1999) pp. 291-295, 27:4 XP002386389.
Namba,M Tsuneo et al., "Studies on dental caries prevention by traditional Chinese Medicines. Screening of crude drugs for inhibitory action on plaque formation," Chemical Abstracts Services (1982) Accession No. 1983:609662.
Kobayashi, Akio et al., "Eugenol and isoeugenol dimers as bactericides, fungicides, and inflammation inhibitors", Chemical Abstracts Services (1997) JP 09167074 Accession No. 1997:580683.
Murakami et al. (Biochemical Pharmacology 66 (2003) 1061-1066).
Mergenhagen et al.( J Dent Res 1970 49: 256-261).
Silverman, Richard B. ("The Organic Chemistry of Drug Design and Drug Action". London: Academic Press Ltd., 1992.).
Baehni, et al. "Anti-plaque agents in the prevention . . ." Oral Diseases (2003) 9, 23-29.
Marsh, "Plaque as a biofilm . . ."Oral Diseases (2003) 9,16-22.
Botelho, "Fractional Inhibitory Concentration . . ."J. of Densistry 28 (2000) 565-570.
Furiga et al. "In Vitro anti-bacterial and anti-adherence" J. Applied Microbiology 2008, 105:1470-1476.
J.M. ten Cate et al. "Procedures for Establishing Efficacy . . ." J. Dent. Res. 73 (3): 695-703, Mar. 1994.

(Continued)

*Primary Examiner* — Frederick Krass
*Assistant Examiner* — Chris Simmons
(74) *Attorney, Agent, or Firm* — Howard C. Lee

(57) ABSTRACT

The invention provides an antiplaque oral composition that includes an orally acceptable carrier; and an antibacterially effective amount of a compound of structure (I)

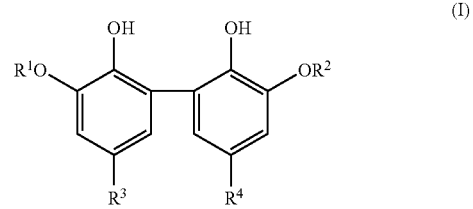

(I)

In the structure, $R^1$ and $R^2$ are independently selected from a lower $C_{1-4}$ alkyl group and $R^3$ and $R^4$ are independently an alkenyl or alkyl group having from 1 to 20 carbon atoms.

Also included in the invention are toothpastes or tooth gels that include at least one humectant: at least one abrasive compound; and an antibacterially effective amount of the compound represented by the structure of formula (I). Also provided are methods of inhibiting bacterial growth in the oral cavity of an animal by application of the compound of formula (I).

25 Claims, No Drawings

OTHER PUBLICATIONS

Delogu et al., 2004, "Enantiopure 2,2'-dihydroxy-3,3'-dimethoxy-5,5'-diallyl-6,6'-dibromo-1,1'-biphenyl: a conformationally stable C2-dimer of a eugenol derivative," Tetrahedron: Asymmetry 15(2):275-282.

Masamichi et al., 2004, "Preparation of Dialkylbisphenols by Oxidative Coupling of p-Alkylphenols," Chemical Abstracts Service STN Database Accession No. 2004:873842.

Asano et al., 1949, Database Beilstein Registry Nos. 3379472, 3424700, 2620747, J. Am. Pharm. Assoc. 38:169-172.

Chiang et al., 1952, Database Beilstein Registry No. 3352973, J. Am. Pharm. Assoc. 41:348-349.

Eistert et al., 1962, "Reactions of Diazoacetic Ester and Diazo-Acetophenone with Di- and Triphenyl-Cyclopentene-Diones," Justus Liebigs Annalen der Chemie 657:120-131.

Evans et al., 1984, "Identification of Fungicidal and Nematocidal Components in the Leaves of the Piper betle (Piperaceae)," J. Agricultural Food Chem. 32:1254-1256.

Ito et al., 2004, "Preparation of Dialyklbisphenols by Oxidative Coupling of p-Alkylphenols," Chemical Abstracts Service STN Database Accession No. 2004:873842.

International Search Report and Written Opinion in International Application No. PCT/US08/078096, mailed Jan. 26, 2009.

Kong et al., 2005, "Cytotoxins Neolignans: an SAR Study," Bioorganic & Medicinal Chemistry Letters 15:163-166.

Liberato et al., 1981, "Regiospecific attack of nitrogen and sulfur nucleophiles on quinones derived from poison oak/ivy catechols (urushiols) and analogues as models for urushiol-protein conjugate formation," J. Med. Chem. 24(1):28-33.

Maruyama et al., 1981, "A Convenient Allylation of Ortho-Quinones. An Extension on the Utility of Allyltin Reagents," Chemistry Letters 10:47-50.

Merriam Webster's Definition for Lozenge, http://www.merriam-webster.com/dictionary/lozenge, 2011.

Ogata et al., 1997, "Antioxidant Activity of Magnolol, Honikiol, and Related Phenolic Compounds," JAOCS 74(5):557-562.

Omote et al., 1976, Database Beilstein Registry No. 2161803, Chemistry and Industry p. 904.

Ramji et al., 2002, "Phenolic Antibacterials from Piper betle in the Prevention of Halitosis," J. Ethnopharmacol. 83:149-152.

Sethi et al., 1964, "Synthesis of 4-Allylcatechol and Mechanism of Claisen Rearrangement in o-Dihydroxy Compounds," Indian J. Chem. 2:323-326.

Zhang, 1999, "Theoretical Methods Used in Elucidating Activity Differences of Phenolic Antioxidants," JAOCS 76(6):745-748.

\* cited by examiner

ANTIBACTERIAL 5,5'-DISUBSTITUTED 3,3' DIALKOXY-2,2'-DIHYDROXY-1,1'-BIPHENYL

CROSS REFERENCE TO RELATED APPLICATION

This application is a continuation of application Ser. No. 11/374,834, filed Mar. 14, 2006, which claims priority to U.S. Provisional Patent Application Ser. No. 60/662,992, filed Mar. 18, 2005, the contents of each which are incorporated herein by reference.

BACKGROUND OF THE INVENTION

A number of disease conditions are associated with the action of bacteria in the oral cavity. Dental plaque is a soft deposit that forms on the surface of the teeth as a by-product of bacterial growth. Gingivitis, an inflammation or infection of the gums and alveolar bones, is generally believed to be caused by plaque causing bacteria and the toxins formed as by-products from the bacteria. In addition, plaque provides a locus for calculus or tartar formation. Periodontitis is generally believed to occur where unremoved plaque hardens into calculus (tartar), which affects the periodontal ligaments. As plaque and tartar continue to build up, the gums begin to recede, which can lead to continued infection and potentially the loss of teeth.

To prevent or treat these diseased conditions, antibacterial agents are incorporated into oral care compositions such as toothpaste and mouthwashes or rinses. Application of antibacterial compositions in the oral cavity tends to retard plaque formation and related oral infections.

The antiplaque efficacy of antibacterial compounds in a dentifrice composition depends on a number of factors, including the presence of other ingredients that may interfere with its action. For example, certain cationic antibacterial compounds and certain nonionic antibacterial compounds lose their effectiveness when formulated with certain anionic surfactants or other anionic active ingredients, such as tartar control phosphates. In many instances, it is preferred to use antibacterial compounds that do not show the adverse interactions with such anionic components.

Some substituted phenols and biphenols are known to have antimicrobial properties. Natural products such as eugenol (4-allyl-2-methoxyphenol) have been used in oral care as a pulp capping agent and root canal sealer. It is generally recognized as safe by the FDA. A dimer of eugenol, dehydrodieugenol, is reported to be less cytotoxic and have greater anti-inflammatory activity than eugenol. There is an ongoing need to find biphenol compounds with acceptable combinations of antibacterial activity and safety.

BRIEF SUMMARY OF THE INVENTION

The invention provides an antiplaque oral composition that includes an orally acceptable carrier, and an antibacterially effective amount of a compound of structure (I):

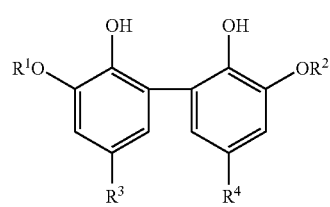

(I)

In the structure, $R^1$ and $R^2$ are independently selected from a lower $C_{1-4}$ alkyl group and $R^3$ and $R^4$ are independently an alkenyl or alkyl group having from 1 to 20 carbon atoms.

Also included in the invention are toothpastes or tooth gels that include at least one humectant; at least one abrasive compound; and an antibacterially effective amount of the compound represented by structure of formula (I):

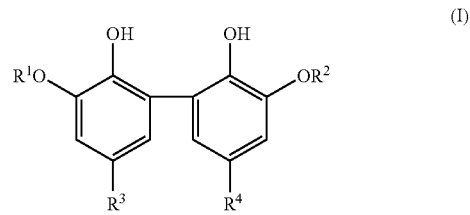

(I)

In (I), $R^1$ and $R^2$ are independently selected from a lower $C_{1-4}$ alkyl group and $R^3$ and $R^4$ are independently an alkenyl or alkyl group having from 1 to 20 carbon atoms.

Also provided are methods of inhibiting bacterial growth in the oral cavity of an animal by application of the compound of formula (I).

DETAILED DESCRIPTION OF THE INVENTION

A class of 5,5'-disubstituted 3,3'-dialkoxy-2,2'-dihydroxy-1,1'-biphenyl compounds exhibits inhibitory action against a variety of bacteria commonly found in the oral cavity. The compounds are used as antiplaque and/or antibacterial components of dentifrices and other oral compositions. The invention provides various oral compositions containing the compounds and an orally acceptable carrier. In various embodiments, antibacterial and antiplaque oral compositions are provided in the form of a toothpaste or gel, a tooth powder, a mouthwash or mouth rinse, a lozenge, chewing gum, an edible strip, and the like. The antibacterial compounds may be conveniently synthesized using novel coupling reaction steps, although any method of synthesis known or to be developed in the art can be used.

The invention provides disubstituted 2,4'-diphenols and derivatives represented by the structure:

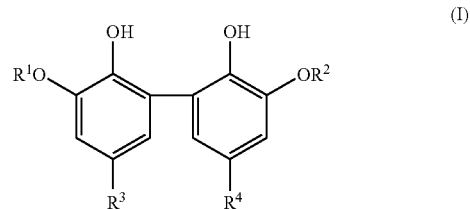

(I)

exclusive of dehydrodieugenol, $R^1$ and $R^2$ are independently a lower $C_{1-4}$ alkyl group and $R^3$ and $R^4$ are independently an alkenyl or alkyl group having from 1 to 20 carbon atoms, with the proviso that $R^3$ and $R^4$ are not both 2-propenyl when $R^1$ and $R^2$ are both $CH_3$. Preferably, R contains 1 to 8 carbon atoms. In various embodiments, R has 4 to 8 carbon atoms.

Antiplaque oral compositions are provided that contain an orally acceptable carrier and an antibacterial effective amount of at least one compound of structure (I). In various embodiments, the compositions contain from about 0.001% to about 10% by weight of (I). Without limitation, the orally acceptable carrier is a liquid earner; a powder carrier; or a carrier that dissolves upon contact with saliva and other components of an oral environment. In other embodiments, the carrier can comprise a gum base. The oral compositions are provided variously in the form of a toothpaste or gel, a tooth powder, a mouthwash or mouth rinse, a lozenge, chewing gum, and an edible strip. Other forms of the composition include without limitation a liquid suitable for painting a dental surface, a wafer, a wipe or towelette, an implant, a dental floss, and forms that are edible or chewable by a small mammal, such as a dog or cat.

In other embodiments, the invention provides toothpaste or gel compositions that contain at least one humectant, at least one abrasive material, and an antibacterial effective amount of at least one compound of structure (I). In various embodiments, the toothpaste or gel compositions further comprise an anticalculus agent such as a phosphate compound, alternatively combined with synthetic anionic polycarboxylates. In an exemplary embodiment, the toothpaste or gel composition comprises 0.001-5% by weight of compound (I);
1-70% by weight humectant;
1-70% by weight abrasive compounds;
0.5-2.5% by weight tetrasodium pyrophosphate (TSPP); and
1-10% by weight sodium tripolyphosphate (STPP).

In other embodiments, the invention provides a method for inhibiting bacterial growth in the oral cavity of a subject animal, human or non-human, comprising applying to the oral surfaces of the subject animal an antibacterial composition comprising at least one compound of structure (I). In various embodiments, the method involves brushing the teeth and rinsing with compositions containing compound (I). As above, the method can be practiced by applying the antibacterial composition in a wide variety of forms such as toothpastes, tooth gels, tooth powder, mouth rinse, mouthwash, paint on gels, dissolvable or edible strips, chewing gum, lozenges, and the like. In various embodiments, treatment of oral surfaces with antibacterial compositions containing the compound of formula (I) may lead to reduction or elimination of plaque, to prevention or treatment of gingivitis, to amelioration of oral malodor, and prevention of periodontal disease.

In various embodiments, the antibacterial compounds are selected from a class of 5,5'-disubstituted-3,3'-dimethoxy-2,2'-dihydroxy-1,1'-biphenyls, represented by the structure:

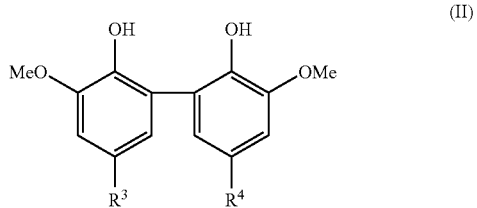

(II)

where $R^3$ and $R^4$ independently represent an alkenyl or alkyl group of 1 to 20 carbon atoms. For example, dehydrodieugenol is the compound where $R^3$ and $R^4$ are 2-propenyl. In various embodiments, the antibacterial compounds are selected from structures (I) and (II) excluding dehydrodieugenol. Structure (II) corresponds to structure (I) where $R^1$ and $R^2$ are both methyl.

In some embodiments of structures (I) and II, both $R^3$ and $R^4$ are alkyl groups. In other embodiments, both $R^3$ and $R^4$ are alkenyl groups. In yet other embodiments, one of the groups $R^3$ and $R^4$ is an alkyl group and the other is an alkenyl group. In various embodiments, the groups $R^3$ and $R^4$ are the same. In various embodiments, oral compositions containing compounds (I) and/or (II) exhibit antibacterial efficacy comparable to compositions containing triclosan.

The size and nature of the alkyl or alkenyl groups $R^3$ and $R^4$ may be selected to achieve a desired combination of solubility and bioavailability in the compounds of structures (I) and (II). The compounds of structure (I) and (II) tend to be lipid soluble; distribution of the compounds between a lipid and water phase is reflected in a value of log P well known to those of skill in the art. In various embodiments, a log P value of 3 to 5 is preferred. In general, the larger the groups $R^3$ and $R^4$ (i.e., the higher the number of carbon atoms in the alkyl or alkenyl groups), the higher the solubility in lipid and the lower the solubility in water. The size of the groups $R^3$ and $R^4$ also affects the molecular weight and thus the molar amount of compounds (I) or (II) delivered by a unit dose. In a preferred embodiment, the groups $R^3$ and $R^4$ are selected such that the solubility of the compound in water is 1 ppm or greater, preferably 5 ppm or greater, and more preferably 10 ppm or greater.

The compound of (I) and (II) may be synthesized by any synthesis pathway known or to be developed in the art. However, an exemplary synthesis of compounds (I) and (II) is illustrated in the following scheme:

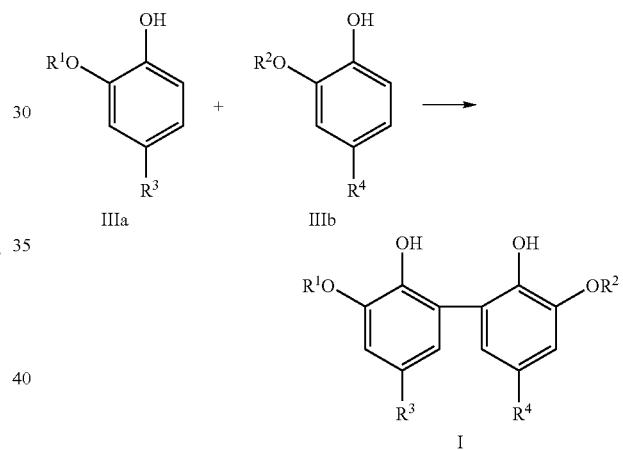

where $R^1$, $R^2$, $R^3$, and $R^4$ are as defined above. A starting material (IIIa) and (IIIb) are reacted under mild oxidizing conditions to give product (I). When (IIIa) and (IIIb) are the same, the reaction is a dimerization that produces a product (I) where $R^1$ and $R^2$ are the same and where $R^3$ and $R^4$ are the same. When (IIIa) and (IIIb) are different, reaction products can be produced where $R^3$ and $R^4$ are different and/or where $R^1$ and $R^2$ are different. In one embodiment, the reaction proceeds in the presence of a ferric compound such as potassium ferrocyanide at room temperature. Suitable solvents include methylene dichloride. In another non-limiting embodiment, oxidative coupling is accomplished by stirring in the presence of a cupric compound such as cupric chloride at room temperature, preferably in the further presence of a mild chelating agent such as N,N,N',N'-tetramethylethylenediamine in suitable solvents such as methylene dichloride.

The antibacterial compound of the invention is formulated together with an orally acceptable carrier to provide oral compositions having a variety of forms such as referred to above. Depending on the form of the composition, the orally acceptable carrier can be a liquid earner, a powder earner, a dissolvable solid carrier, a gum base, a film forming polymer or polymers, and so on.

Various compositions of the invention contain an orally acceptable carrier and an antibacterial effective amount of compound (I) and/or (II). The effective amount is in the form of either a single compound or a mixture of compounds represented by structure (I) and/or (II). A mixture of compounds can result for example from intentional addition of separately synthesized compounds or from addition of a reaction product containing a mixture of substitution patterns of the groups $R^1$, $R^2$, $R^3$, and $R^4$.

As used herein, the "carrier" refers to components of the individual oral compositions in which the antibacterial compound or compounds of structure (I) are formulated as an active ingredient. In various embodiments, the carrier encompasses all of the components of the oral composition except for the antibacterial compound (I). In other aspects, the term refers to components such as inactive ingredients, carriers, vehicles, and the like, that are commonly understood to persons of skill in the art to function as a carrier, filler or other relatively inert ingredient. In other words, the term carrier is used in different ways depending on context. Depending on the context, the oral compositions comprise other components in addition to the active compound (I) and/or (II) and the carrier. However, in all contexts, the components of the oral compositions of the invention can be divided into carrier components and the antibacterial compounds (I) and/or (II).

To illustrate in a non-limiting example for the case of toothpastes, the carrier can be said to be the water/humectant system that provides a large fraction by weight of the composition. Alternatively, the carrier component of a toothpaste composition may be considered as the water, humectant, and other functional components other than the antibacterial system. Whatever the context, the person of skill in the art recognizes that the toothpaste composition contains antibacterial compounds (I) and/or (II) and an orally acceptable carrier for the compound(s).

For example in a mouth rinse, the carrier is generally considered to be the water/alcohol liquid component in which the antibacterial compounds (I) are dissolved or dispersed. In a dissolvable lozenge, the carrier is generally understood to comprise the solid matrix material that dissolves slowly in the mouth to the oral surfaces in the mouth. In chewing gums, the carrier comprises a gum base, while in an edible strip, the carrier comprises one or more film forming polymers.

In all of the above examples, the oral composition, in whatever form, includes antibacterial compounds (I) and/or (II), a suitable carrier in an appropriate form, and other actives or functional materials needed to provide the oral compositions with desired properties. Additional active materials and functional materials are described below.

In addition to a biologically acceptable earner, oral compositions of the invention contain an antibacterial effective amount of compound (I) and/or (II). In various embodiments, an antibacterial effective amount is from about 0.001% to about 10%, based on the total weight of the oral composition, for example from 0.01% to about 5% or about 0.1% to about 2%. The effective amount will vary depending on the form of the oral composition. For example, in toothpastes, tooth gels, and tooth powders, an effective amount is usually at least about 0.01% and more preferably at least about 0.05%. In some preferred embodiments, compound (I) is present in a toothpaste, gel, or powder at a level of 0.1% or more, to achieve a desired level of antibacterial activity. Normally, compound (I) and/or (II) is formulated at 5% or less, preferably about 2% or less, and more preferably about 1% or less. Concentrations in the upper end of these limits can be used, but are sometimes less preferred for economic reasons. In various embodiments, optimum effectiveness may be achieved at from about 0.1% to about 1%, especially from about 0.1% to about 0.5% or about 0.1% to about 0.3%, wherein all percentages are based on the total weight of the oral composition. Amounts used in tooth gels, tooth powders, gums, edible strips, and the like are comparable to those used in toothpastes.

In mouth washes and rinses, an antibacterial effective amount of the compound represented by formula (I) and/or (II) is normally on the lower side of the above ranges. Typically, compound (I) and/or (II) is used at a level of about 0.001% (or 10 ppm) up to about 1% or less. Preferably, compound (I) and/or (II) is at about 0.5% or less or about 0.2% or less. Preferably it is about 0.01% (100 ppm) or greater. In various embodiments, compound (I) and/or (II) is present at from 0.03 to 0.12% by weight.

The statements herein for structure (I) also apply to structure (II), which illustrates an embodiment or species of structure (I) where $R^1$ and $R^2$ are both hydrogen atoms. In addition to the antibacterial compound (I), a number of active ingredients and functional materials are included in various compositions of the invention. Such materials include, without limitation, abrasives, humectants, surfactants, anticalculus agents, thickeners, viscosity modifiers, anticaries agents, flavorants, colorants, additional antibacterial agents, antioxidants, anti-inflammation components, and so on. They are added to the pastes, rinses, gums, lozenges, strips, and other forms of the oral compositions of the invention according to known methods.

In various embodiments of the present invention, where the carrier of the oral care composition is solid or a paste, the oral composition preferably comprises a dentally acceptable abrasive material, which serves to either polish the tooth enamel or provide a whitening effect. Non-limiting examples include silica abrasives such as silica gels and precipitated silicas. Commercial embodiments include ZEODENT® 115, marketed by J. M. Huber, Edison, N.J., United States of America, and SYLODENT® XWA, SYLODENT® 783 or SYLODENT® 650 XWA of the Davison Chemical Division of W. R. Grace & Co., New York, N.Y., United States of America. Other useful dentifrice abrasives include, without limitation, sodium metaphosphate, potassium metaphosphate, tricalcium phosphate, dihydrated dicalcium phosphate, aluminum silicate, calcined alumina, bentonite or other siliceous materials, or combinations thereof.

The abrasive is present in an effective amount. In embodiments where the oral composition is in a solid or paste form, the abrasive material is generally present at about 10% to about 99% of the oral composition. In certain embodiments, the polishing material is present in amounts ranging from about 10% to about 75% (for example about 10% to about 40% or about 15% to about 30%) in toothpaste, and from about 70% to about 99% in toothpowder.

In a still further embodiment a composition of the invention comprises at least one humectant, useful for example to prevent hardening of a toothpaste upon exposure to air. Any orally acceptable humectant can be used, including without limitation polyhydric alcohols such as glycerin, sorbitol, xylitol and low molecular weight PEGs. Most humectants also function as sweeteners. One or more humectants are optionally present in a total amount of about 1% to about 70%, for example about 1% to about 50%, about 2% to about 25%, or about 5% to about 15% by weight of the composition.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates, and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01% to about 10%, for example about 0.05% to about 5% or about 0.1% to about 2% by weight of the composition.

In another embodiment, the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example the alkali metal and ammonium salts. Useful inorganic phosphate and polyphosphate salts illustratively include monobasic, dibasic and tribasic sodium phosphates, sodium tripolyphosphate (STPP), tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include polycarboxylate polymers. These include polymers or copolymers of monomers that contain carboxylic acid groups, such as acrylic acid, methacrylic acid, and maleic acid or anhydride. Non-limiting examples include polyvinyl methyl ether/maleic anhydride (PVME/MA) copolymers, such as those available under the GANTREZ® brand from ISP, Wayne, N.J., United States of America. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically about 0.01% to about 50%, for example about 0.05% to about 25% or about 0.1% to about 15% by weight.

In various embodiments, the anticalculus system comprises a mixture of sodium tripolyphsophate (STPP) and a tetrasodium pyrophosphate (TSPP). In various embodiments, the ratio of TSPP to STPP ranges from about 1:2 to about 1:4. In a preferred embodiment, the first anticalculus active ingredient, TSPP is present at about 1 to about 2.5% and the second anticalculus active ingredient, STPP is present at about 1 to about 10%.

In various embodiments, the anticalculus system further comprises a synthetic anionic polycarboxylate polymer. In one embodiment, the synthetic anionic polycarboxylate is present from about 0.1% to about 5%. In another embodiment, the synthetic anionic polycarboxylate is present from about 0.5% to about 1.5%, most preferably at about 1% of the oral care composition. In one embodiment according to the present invention, the anticalculus system comprises a copolymer of maleic anhydride and methyl vinyl ether, such as for example, the GANTREZ® S-97 product discussed above.

In various embodiments, the ratio of TSPP to STPP to the synthetic anionic polycarboxylate ranges from about 5:10:1 to about 5:20:10 (or 1:4:2). In one embodiment, the anticalculus system of the oral care composition comprises TSPP, STPP, and a polycarboxylate such as a copolymer of maleic anhydride and methyl vinyl ether at a ratio of about 1:7:1. In a non-limiting embodiment, the anticalculus system consists essentially of TSPP present at about 0.5% to about 2.5%, STPP present at about 1% to about 10%, and a copolymer of maleic anhydride and methyl vinyl ether present at about 0.5% to about 1.5%.

In a still further embodiment a composition of the invention comprises at least one thickening agent, useful for example, to impart a desired consistency and/or mouth feel to the composition. Any orally acceptable thickening agent can be used, including without limitation carbomers, also known as carboxyvinyl polymers, carrageenans, also known as Irish moss and more particularly i-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

In a still further embodiment a composition of the invention comprises at least one viscosity modifier, useful for example, to inhibit settling or separation of ingredients or to promote redispersibility upon agitation of a liquid composition. Any orally acceptable viscosity modifier can be used, including without limitation mineral oil, petrolatum, clays and organo-modified clays, silica, and the like. One or more viscosity modifiers are optionally present in a total amount of about 0.01%) to about 10%, for example about 0.1% to about 5% by weight of the composition.

In another embodiment, the composition comprises an orally acceptable source of fluoride ions. One or more such sources can be present. Suitable sources of fluoride ions include fluoride, monofluorophosphate and fluorosilicate salts, and amine fluorides, including olaflur (N'-octadecyltrimethylendiamine-N,N,N'-tris(2-ethanol)-dihydrofluoride). Any such salt that is orally acceptable can be used, including without limitation alkali metal (e.g., potassium, sodium), ammonium, stannous and indium salts, and the like. Water-soluble fluoride-releasing salts are typically used. One or more fluoride-releasing salts are optionally present in an amount providing a total of about 100 to about 20,000 ppm, about 200 to about 5,000 ppm, or about 500 to about 2,500 ppm, fluoride ions. Where sodium fluoride is the sole fluoride-releasing salt present, illustratively an amount of about 0.01%) to about 5%, about 0.05% to about 1% or about 0.1% to about 0.5%, sodium fluoride by weight can be present in the composition.

Other components include, without limitation, flavorants, colorants, and other active ingredients such as antioxidants and anti-inflammation agents. The components are formulated into oral compositions according to known procedures.

Toothpastes and gels contain major amounts of humectants and usually an abrasive compound or compounds for teeth cleaning. They are formulated with various active ingredients, such as anticaries agents, antiplaque compound, anti-inflammation agents, and the like, in addition to the antibacterial compound (I).

Mouth rinses and mouth washes contain the active compound (I) in a liquid carrier such as water or water/ethanol. Generally, the compositions contain a major amount of solvent, up to 98 or 99% by weight. The active compound (I) is optionally formulated together with surfactants, colorants, flavorants, and other active ingredients.

The orally acceptable vehicle or carrier in a lozenge bead or tablet is a non-cariogenic, solid water-soluble polyhydric alcohol (polyol) such as mannitol, xylitol, sorbitol, malitol, hydrogenated starch hydrozylate, hydrogenated glucose, hydrogenated disaccharides, hydrogenated polysaccharides, and the like in an amount of about 85% to about 95% of the total composition. Emulsifiers such as glycerin, and tableting lubricants, in minor amounts of about 0.1% to 5%, may be incorporated into the tablet, bead or lozenge formulation to facilitate the preparation of the tablet beads and lozenges. Suitable lubricants include vegetable oils such as coconut oil, magnesium stearate, aluminum stearate, talc, starch and Carbowax. Suitable non-cariogenic gums include kappa carrageenan, carboxymethyl cellulose, hydroxyethyl cellulose, and the like.

The lozenge, bead or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the antibacterial and anticalculus active ingredients of the present invention.

Chewing gum formulations typically contain a chewing gum base, one or more plasticizing agents, at least one sweetening agent and at least one flavoring agent, in addition to antibacterial compound (I). It is preferably a sugarless gum.

Gum base materials are well known in the art and include natural or synthetic gum bases thereof. Representative natural gums or elastomers include chicle, natural rubber, jelutong, balata, guttapercha, lechi caspi, sorva, guttakay, crown gum, and perillo, or mixtures thereof. Representative synthetic gums or elastomers include butadiene-styrene copolymers, polyisobutylene and isobutylene-isoprene copolymers. The gum base is incorporated in the chewing gum product at a concentration of about 10% to about 40% and preferably about 20% to about 35%.

Plasticizing/softening agents include without limitation gelatin, waxes and mixtures thereof in amounts of about 0.1% to about 5%. The sweetening agent ingredient used in the practice of this invention may be selected from a wide range of materials, and include the same artificial and polyol sweeteners used for the preparation of tablets, beads and lozenges. Polyol sweeteners such as sorbitol and malitol are present in the chewing gum composition of the present invention in amounts of about 40% to about 80% and preferably about 50% to about 75%. In a non-limiting embodiment, an artificial sweetener is present in the chewing gum composition of the present invention in amounts of about 0.1% to about 2% and preferably about 0.3% to about 1%.

I claim:

1. An antiplaque oral composition comprising
an orally acceptable carrier; and
an antibacterially effective amount of a compound of structure (I)

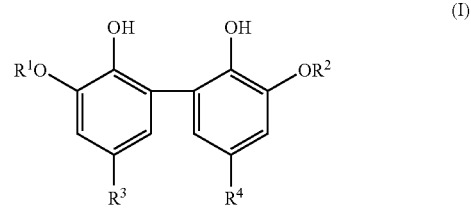

wherein $R^1$ and $R^2$ are independently a lower $C_{1-4}$ alkyl group and $R^3$ and $R^4$ are independently an alkenyl or alkyl group having from 1 to 20 carbon atoms' wherein the compound of structure (I) is not dehydrodieugenol.

2. The composition of claim 1, comprising 0.001% to 10% by weight of the compound of formula (I).

3. The composition of claim 1, wherein the carrier is a liquid carrier.

4. The composition of claim 1, wherein the carrier is a powder carrier.

5. The composition of claim 1, wherein the carrier dissolves upon contact with an oral environment.

6. The composition of claim 1 in a form selected from a paste, a gel, a powder, a mouth rinse, a lozenge, a chewing gum, and an edible strip.

7. The composition of claim 1, wherein $R^1$ and $R^2$ independently are methyl.

8. The composition of claim 1, wherein $R^3$ and $R^4$ independently are alkyl.

9. The composition of claim 1, wherein $R^3$ and $R^4$ independently have 1 to 8 carbon atoms.

10. The composition of claim 1, wherein $R^3$ and $R^4$ independently have 4 to 8 carbon atoms.

11. A toothpaste or gel composition comprising
at least one humectant:
at least one abrasive compound; and
an antibacterially effective amount of a compound of structure (I)

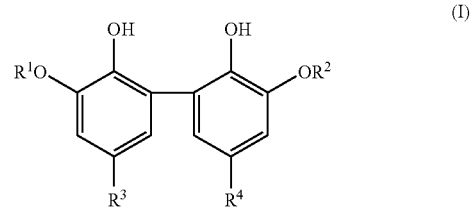

wherein $R^1$ and $R^2$ are independently a lower $C_{1-4}$ alkyl group and $R^3$ and $R^4$ are independently an alkenyl or alkyl group having from 1 to 20 carbon atoms, wherein the compound of structure (I) is not dehydrodieugenol.

12. The composition of claim 11, further comprising an anti tartar effective amount of an anticalculus agent comprising at least one phosphate compound.

13. The composition of claim 12, wherein the anticalculus agent comprises tetrasodium pyrophosphate and trisodium polyphosphate.

14. The composition of claim 13, wherein the anticalculus agent further comprises a synthetic anionic polycarboxylate.

15. The composition of claim 14, wherein the synthetic anionic polycarboxylate comprises a maleic anhydride copolymer with methyl vinyl ether.

16. The composition of claim 12, comprising 0.01-5% by weight of a compound of structure (I);

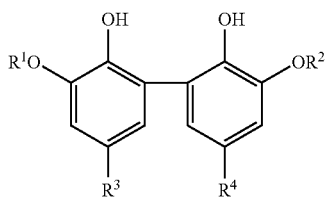

(I)

1-70% by weight or at least one humectant;

1-70% by weight of an abrasive compound;

0.5-2.5% by weight of tetrasodium pyrophosphate (TSPP); and 1-10% by weight of sodium tripolyphosphate (STPP).

17. The composition of claim 16, wherein the weight ratio of TSPP:STPP is about 1:7.

18. The composition of claim 16, further comprising an anionic polycarboxylate.

19. The composition of claim 18, wherein the ratio of TSPP:STPP:polycarboxylate is about 1:7:1.

20. A method for inhibiting bacterial growth in the oral cavity of an animal, comprising applying to the oral surfaces of the subject animal an antibacterial composition comprising a compound of structure (I)

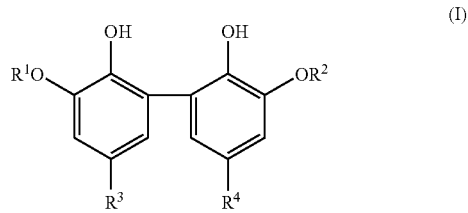

(I)

wherein $R^1$ and $R^2$ are independently a lower $C_{1-4}$ alkyl group and $R^3$ and $R^4$ are independently an alkenyl or alkyl group having from 1 to 20 carbon atoms, wherein the compound of structure (I) is not dehydrodieugenol.

21. The method of claim 20, wherein application comprises brushing the teeth.

22. The method of claim 20, wherein applying comprises rinsing the oral surfaces with the composition, wherein the composition is in the form of a mouth rinse.

23. The method of claim 20, wherein the antibacterial composition is a toothpaste or gel.

24. The method of claim 20, wherein the antibacterial composition is a mouth rinse.

25. The method of claim 20, wherein the animal is selected from an equine species, a feline species, a canine species, and a human.

* * * * *